US012779593B2

(12) United States Patent
Neckin et al.

(10) Patent No.: US 12,779,593 B2
(45) Date of Patent: Nov. 3, 2026

(54) LASER CUTTING SYSTEM AND BEAM BLOCK FOR SUCH SYSTEM

(71) Applicant: BIOTRONIK AG, Bülach (CH)

(72) Inventors: André Neckin, Rostock (DE); Ralf Klemm, Parkentin (DE); André Burgschat, Rostock (DE); Ole Graentzel, Rostock (DE); Gilbert Schacht, Rostock (DE)

(73) Assignee: BIOTRONIK AG, Bülach (CH)

( * ) Notice: Subject to any disclaimer, the term of this patent is extended or adjusted under 35 U.S.C. 154(b) by 588 days.

(21) Appl. No.: 18/452,026

(22) Filed: Aug. 18, 2023

(65) Prior Publication Data

US 2024/0131628 A1 Apr. 25, 2024
US 2024/0227082 A9 Jul. 11, 2024

(30) Foreign Application Priority Data

Oct. 19, 2022 (EP) .................................... 22202430

(51) Int. Cl.
*B23K 26/38* (2014.01)
*B23K 26/0622* (2014.01)
(Continued)

(52) U.S. Cl.
CPC .......... *B23K 26/38* (2013.01); *B23K 26/0622* (2015.10); *A61F 2/82* (2013.01); *A61F 2240/001* (2013.01); *B23K 2101/06* (2018.08)

(58) Field of Classification Search
CPC ............ B23K 2101/04; B23K 2101/06; B23K 26/14; B23K 26/142; B23K 26/16; B23K 26/38; B26K 37/06
See application file for complete search history.

(56) References Cited

U.S. PATENT DOCUMENTS 5,994,667 A * 11/1999 Merdan .................. B23K 26/18
219/121.7
2004/0089643 A1 5/2004 Jones et al.
(Continued)

FOREIGN PATENT DOCUMENTS

CN 210818000 U * 6/2020 ............. B23K 26/38
JP S60166184 A * 8/1985 ............. B23K 26/00
WO 2022093537 A1 5/2022

OTHER PUBLICATIONS

English translation of CN210818000U (Year: 2020).*
(Continued)

*Primary Examiner* — Scott J Walthour
(74) *Attorney, Agent, or Firm* — Greer, Burns & Crain, Ltd.; Steven P. Fallon

(57) ABSTRACT

A beam block for laser cutting to produce a perforated tubular workpiece includes a tubular head section configured to be accommodated within an inner cavity of a semi-finished product during laser cutting, The tubular head section includes a recess at its first end configured to accept molten workpiece material into an inner surface of the tubular head section. A shaft section is located at a second end of the tubular head section. A plunger is configured to be reciprocated along an inner cavity of the tubular head section inner to the first end of the tubular head section to thereby eject molten workpiece material from the inner surface of the tubular head section. The plunger can be reciprocated periodically during laser cutting to eject molten workpiece material.

17 Claims, 3 Drawing Sheets

(51) Int. Cl.
*A61F 2/82* (2013.01)
*B23K 101/06* (2006.01)

(56) References Cited

U.S. PATENT DOCUMENTS

2010/0193485 A1* 8/2010 Anukhin ................ B23K 26/40 219/121.72
2023/0083702 A1* 3/2023 Lau ......................... A61L 29/18 219/121.63

OTHER PUBLICATIONS

English translation of JPS60166184A (Year: 1985).*
European Search Report from the corresponding European Patent Application No. EP 22202430.9, dated Apr. 14, 2023.

* cited by examiner

LASER CUTTING SYSTEM AND BEAM BLOCK FOR SUCH SYSTEM

PRIORITY CLAIM

This application claims priority under 35 U.S.C. § 119 and all applicable statutes and treaties from prior European Application No. EP 22202430.9, which was filed Oct. 19, 2022.

FIELD OF THE INVENTION

A field of the invention is laser cutting systems. The invention particularly concerns laser cutting systems that can fabricate a small perforated tubular workpiece, such as a stent or stent structure.

BACKGROUND

Small perforated tubular workpieces such as stents or stent structures are often produced by laser cutting from a tubular semi-finished product, which may be a full or a partly full tube. A stent or a stent structure is a perforated metal or plastic tube that may be inserted (implanted) into the lumen of an anatomic vessel or duct of a human being or an animal to keep the passageway open or to fix an implant at the inner wall of the vessel such as an artificial valve. There are a wide variety of stents or stent structures used for different purposes, for example, mechanical stents or stent structures, balloon-expandable stents, and/or self-expanding coronary or peripheral stents, vascular and biliary stents, stent grafts or covered stents (covered with fabric or biological material, for example, cellulose, bacterial cellulose or biological tissue, for example, pericardium or treated pericardium), prosthetic heart valve stents, ureteral stents, prostatic stents, colon and esophageal stents, pancreatic and biliary stents, and glaucoma drainage stents and occluder, for example LAA-occluder.

During laser processing of such perforated tubular workpieces, the laser cuts through the material of the semi-finished product thereby producing small structures having a diameter of, for example, less than a tenth of a millimeter such as holes, struts, webs, wires and web/strut connection, i.e. the perforated structure. A laser cutting system for such small structures typically uses a microsecond pulsed laser that perform a melt cutting process (also referred to as fusion cutting process). In such process the material is heated to its melting point and a gas jet blows the molten material out of the kerf limiting the raise the temperature of the material and avoiding oxidation at the area of the cut. As the semi-finished product is a tube or a partly full tube, a beam block is accommodated within the inner cavity of the tube to focus laser machining to the one of the opposing tube walls that is closest to the laser nozzle and avoid undesirable laser process induced material alterations of the respective opposite tube wall.

A beam block located within the workpiece may have the form of a cylinder, a tube or a section of such cylinder or tube. The above-described melt and blow process of molten material causes deposition of molten material at the surface of such beam block that may accumulate and attach to the surface of the beam block so that the gas jet cannot or cannot fully remove such materials accumulation. The accumulated material may contact the inner surface of the workpiece during laser processing thereby causing dimensional deviations and/or defects at the inner surface of the workpiece and workpiece rejects.

SUMMARY OF THE INVENTION

A beam block for laser cutting to produce a perforated tubular workpiece includes a tubular head section configured to be accommodated within an inner cavity of a semi-finished product during laser cutting. The tubular head section includes a recess at its first end configured to accept molten workpiece material into an inner surface of the tubular head section. A shaft section is located at a second end of the tubular head section. A plunger is configured to be reciprocated along an inner cavity of the tubular head section inner to the first end of the tubular head section to thereby eject molten workpiece material from the inner surface of the tubular head section. The plunger can be reciprocated periodically during laser cutting to eject molten workpiece material.

BRIEF DESCRIPTION OF THE DRAWINGS

The various features and advantages of the present invention may be more readily understood with reference to the following detailed description and the embodiments shown in the drawings, of which.

DETAILED DESCRIPTION OF THE PREFERRED EMBODIMENTS

Figure 1:
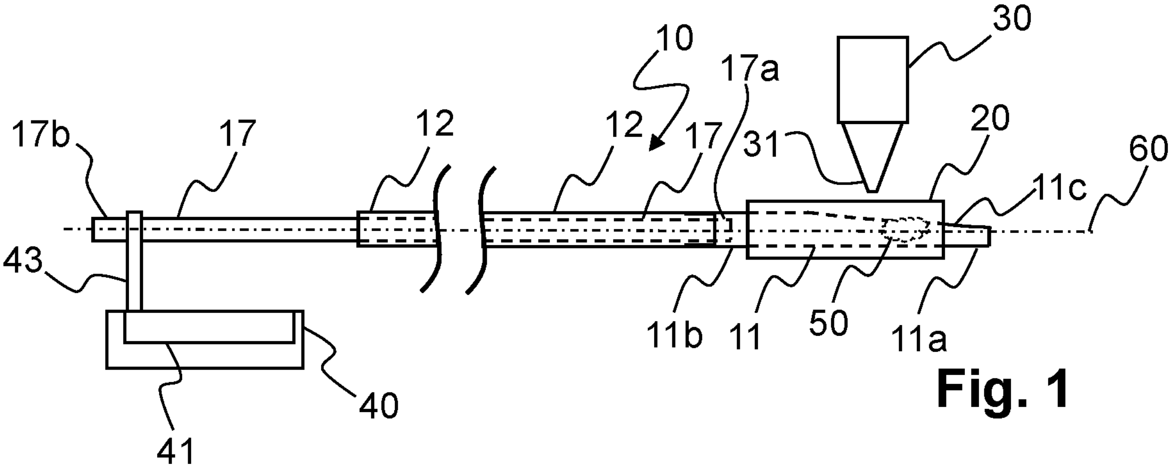
FIGS. 1 to 3 depict a first embodiment of a laser cutting system with a first embodiment of a beam block in a side view in three different operation states.

The invention is directed to a beam block for laser cutting to produce a perforated tubular workpiece, for example a stent or a stent structure, from a tubular semi-finished product, an operation method of such beam block, a laser cutting system including such beam block, a manufacturing method for such perforated tubular workpiece using such laser cutting system, and a workpiece manufactured according to such manufacturing method.

In particular, a preferred beam block for laser cutting to produce a perforated tubular workpiece, for example a stent or a stent structure, from a tubular semi-finished product includes

- a tubular head section configured to be accommodated within a semi-finished product inner cavity during laser cutting, wherein the tubular head section has a recess at its first end that allows depositing molten workpiece material at an inner surface of the head section,
- a shaft section located at a second end of the tubular head section, and
- a plunger element configured to be reciprocated along a head section inner cavity to the first end of the tubular head section thereby ejecting molten workpiece material deposited at an inner surface of the head section.

The above beam block is used for laser cutting a tube or a partly full tube of a semi-finished product by a melt cutting process as indicated above using a microsecond pulsed laser. Preferably, the microsecond pulsed laser has an emission wavelength in the Near-Infrared, for example, within the range of 1000 to 1100 nm. Such laser may be, for example, a fiber laser emitting in the Near-Infrared. The above beam block is used to manufacture laser cut perforated tubular workpieces such as stents or stent structures, e.g. expandable coronary, vascular and biliary stents, stent grafts or covered stents (covered with fabric), ureteral stents, prostatic stents, colon and esophageal stents, pancreatic and biliary stents, and glaucoma drainage stents.

The beam block includes a head section and a shaft section, wherein the shaft section is fixed to the head section at the second end of the head section. The head section forms the seat for the tubular semi-finished product during laser cutting, i.e. the semi-finished product located at the tubular head section of the beam block in the area of the first end and the recess. The tubular head section is slid into the inner cavity of the semi-finished product prior laser cutting. During the laser cutting process the tube wall closest to the laser and its nozzle is cut, the beam block blocks the laser beam and thereby avoids that the laser produces material alterations at the opposite tube wall. The recess runs at least partly inclined with regard to the longitudinal axis of the tubular head section and is provided such that a part of the head section wall is removed, wherein the removed part is enlarged into the direction of the first end of the head section. Due to the removal of a part of the head section wall, the gas jet of the laser intrudes into the inner cavity of the head section of the beam block. Accordingly, during laser cutting the gas jet transports molten material of the workpiece removed by the laser and the gas jet. This molten material accumulates at the inner surface of the inner cavity of the head section.

According to the invention this molten material is removed by the plunger element that reciprocates to the first end along the head section inner cavity. For example, the initial position of the leading end (first end) of the plunger element is at the second end of the beam block head section, so that it reciprocates from the second end to the first end along the head section inner cavity.

The invention provides a cost-effective, fast and easy to realize removal of the molten material thereby considerably reducing the reject of perforated tubular workpieces. A test production of laser cut stents using the above described beam block revealed a reduction to about one third of rejected stents. Accordingly, as less workpieces need to be sorted out due to incorrect dimensions, material expenses as well as laser cutter running time are reduced. This leads to reduction of personnel costs and quality check costs, as well.

In one embodiment, the plunger element has a simple and easy to realize wire-like or cylindrical form, at least at its leading end (first end), that moves with little play within the inner cavity of the head section of the beam block. In one embodiment, the plunger element has a wire-like form along its full length. The outer diameter of the plunger element leading end reaching the very first end of the head section during reciprocating movement is provided such that it is little less than the inner diameter of the inner cavity of the head section of the beam block. In one embodiment, the plunger element has this outer diameter along its full length. During reciprocating movement the plunger element moves forward to the first end (i.e. during the forward movement phase of the reciprocating movement), thereby it scrapes off the molten workpiece material accumulated at the inner surface of the head section inner cavity and pushes the molten workpiece material to the very first end of the head section so that it falls out of the head section inner cavity into a collecting box or into a ready cut section of the tubular semi-finished product which overhangs the very first end of the head section, and from there into the collecting box. In the collecting box the molten material is collected and may be recycled lateron. Then, the plunger element moves backward (i.e. during the backward movement phase of the reciprocating movement) from the first end back to its initial position, e.g. to the second end of the beam block head section. The plunger element may have a length that is about the length of the beam block head section and shaft section or greater. The realization of the reciprocating movement of the plunger element is cost-effective and easy to control.

The plunger element may include or consist of a metal material, for example V2A steel. The beam block head section and/or shaft section may include or consist of a metal material, for example a thermally stable alloy. These materials effectively block the laser radiation and reliably provide the scraping and pushing function with regard to the molten material collecting at the inner cavity of the beam block head section, respectively.

As indicated above, in one embodiment of the beam block, the plunger element has a wire-like form and/or is connected to and driven by a pneumatic, electric or hydraulic driving unit, wherein the driving unit includes, for example, a pneumatic cylinder, e.g. a double acting pneumatic cylinder. The plunger element may be connected to the driving unit, for example, by a web-like element. Such driving unit reliably moves the plunger element and is easy controllable.

In one embodiment of the beam block, the shaft section has a tubular form and/or the plunger element reciprocates along the shaft section. In one embodiment, the head section is fixed to the shaft section by an adhesive joint. For example, the adhesive joint of the head section is formed by a section of the outer shell surface at the second end of the head section to which an inner surface of the inner cavity of the shaft section is fixed. Alternatively, vice versa an outer shell surface of the shaft section is fixed to an inner surface of the inner cavity of the head section of the beam block. In an alternative embodiment, the head section may be fixed to the shaft section by a positive and/or friction locking connection. It is important, that the inner cavities of the head section and the shaft section form a continuous cavity in which the plunger element extending along the head and shaft section may smoothly reciprocate. As indicated above, the plunger element length may greater than the longitudinal length of the head and shaft section of the beam block. It extends from the end of the shaft section of the beam block where it is connected to the driving unit. The above-described construction of the beam block provides reliable reciprocating movement of the plunger element within the inner cavity of the shaft and head section of the beam block due to a correct guidance.

In one embodiment, the beam block includes a tubular sleeve accommodated at a part of the shell surface of the head section of the beam block having a non-stick shell surface. In one embodiment, the tubular sleeve includes or consist of Polytetrafluoroethylene (PTFE) forming the non-stick shell surface. The tubular sleeve is fixed to the outer shell surface of the head section by an adhesive joint. The tubular sleeve smoothens the gliding/sliding of the beam block along a guiding surface, for example during introduction into the semi-finished product prior lasering. The beam block may include two or more of such tubular sleeves along its entire length, along its head and shaft section. Additionally or alternatively, there may be a PTFE block including a through-going opening as a guide for the shaft section of the beam block which also provides a reliable non-sticking guidance of the beam block.

In one embodiment of the beam block, the driving unit includes a damping component configured to damp the plunger element movement at the end of at least one of the forward movement phase and the backward movement phase of the reciprocating movement. For example, the damping may be realized by a throttle check valve. The damping avoids transfer of vibrations caused by the plunger element movement to the semi-finished product thereby preventing accuracy reduction of laser cutting and increases the operation lifetime of the pneumatic cylinder.

Further, the above problem is solved by a laser cutting system including the above-described beam block and a laser cutter, wherein the head section of the beam block is configured to be accommodated within a tubular semi-finished product to be cut by the laser cutter, wherein a nozzle of the laser cutter is located within a pre-defined radial distance from an outer shell surface of the semi-finished product. The laser cutter may include a laser providing μs pulses with an excitation wavelength in the Near-Infrared, for example in the range between 1000 nm to 1100 nm. The high pressure process gas for cutting may be, for example, argon. In one embodiment, the cutting velocity may be 20 mm/s or less. The radial distance of the laser cutter from the surface of the semi-finished product may be, for example, in between one and five tenths of a millimeter. Similar to the beam block, the laser cutting system reduces productions costs for perforated tubular workpieces.

Further, the above problem is solved by an operation method of above-described beam block, wherein the plunger element is reciprocated along the head section inner cavity to the first end of the tubular head section thereby ejecting molten workpiece material deposited at an inner surface of the head section. As indicated above, the plunger element moves in a forward movement phase to the very first end of the head section of the beam block thereby scraping the deposited molten material from the inner surface of the head section, pushing it to the first end of the head section so that it falls out of the inner cavity. The above operation method realizes a method that is cost effective also because it does not need any additional time as it may be used during laser cutting of the semi-finished product.

In one embodiment of the operation method, the plunger element is periodically reciprocated having a frequency in the range of 0.2 $min^{-1}$ to 0.0055 Hz. This frequency was proven to remove the accumulated molten material during laser cutting in a sufficient way during test production. Depending on the speed of the laser cutting and of the thickness of the wall of the tubular semi-finished product the frequency may be even lower or higher than 0.2 $min^{-1}$ to 0.0055 Hz. The same applies to the embodiment of the operation method, wherein the duration of one reciprocating movement of the plunger element is in the range of 0.5 s to 10 s, preferably in the range of 0.5 s to 1.5 s.

In one embodiment of the operation method, the reciprocating movement of the plunger element is damped at the end of at least one of the forward movement phase and the backward movement phase of the reciprocating movement. As indicated above, the damping reduces vibrations that may otherwise be transferred to the semi-finished product during lasering and may interfere with laser cutting.

Furthermore, the above problem is solved by a manufacturing method for a perforated tubular workpiece from a tubular semi-finished product using the above-described laser cutting system and including the following steps:

accommodating the beam block within the semi-finished product such that the product is located within the area of the first end of the tubular head section, laser cutting the semi-finished product using the laser cutter, and operating the beam block according to the above-described operation method.

In one embodiment, the laser cutting is provided by the laser as described above, for example using the melt cutting process. The laser cuts perforations such that structures are formed in wall of the tubular semi-finished product, wherein the perforations are cut through the whole wand thickness of the semi-finished product. The structures are, for example, holes, struts, webs, wires and web/strut connections or similar structures including any combination of these structures. In one embodiment, the plunger element reciprocating movement of the beam block operation is provided periodically during laser cutting the semi-finished product. I.e. the beam block, in particular the plunger element, is operated, for example, during laser cutting of the semi-finished product with a frequency as indicated above. Each molten material removal step, i.e. each reciprocated movement has the duration as disclosed above. The manufacturing method includes the above advantages of the beam block and its operation method as well as of the laser cutting system.

The above problem is further solved by a perforated tubular workpiece, e.g. a stent, manufactured from a tubular semi-finished product according to above-described manufacturing method that may be produced in a considerable cost-effective way. The tubular workpiece includes perforations cut by the laser cutter through the whole wand thickness of the semi-finished product such that remaining structures, for example, holes, struts, webs, wires, web/strut connections or similar structures including any combination of these structures are produced. The semi-finished product and the tubular workpiece may include or consist of a biocompatible material, for example Nitinol.

Figure 2:
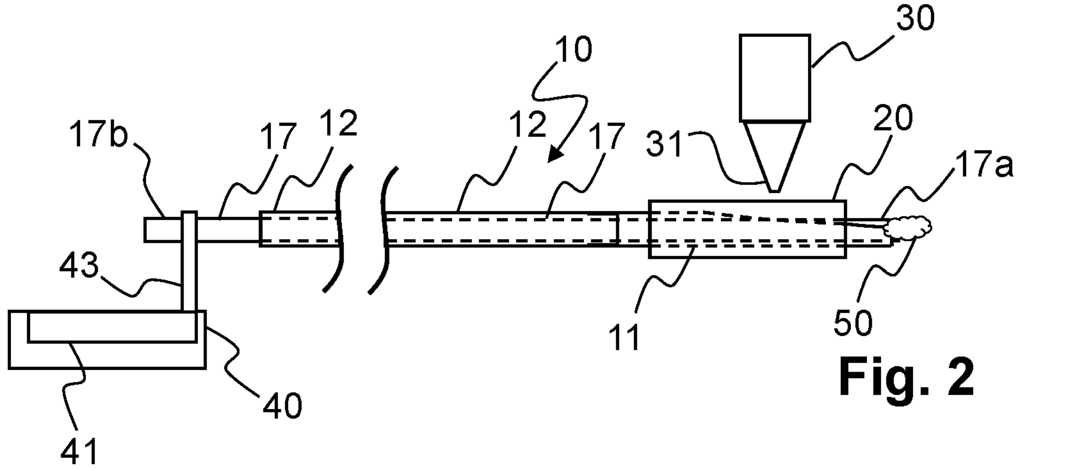
Figure 3:
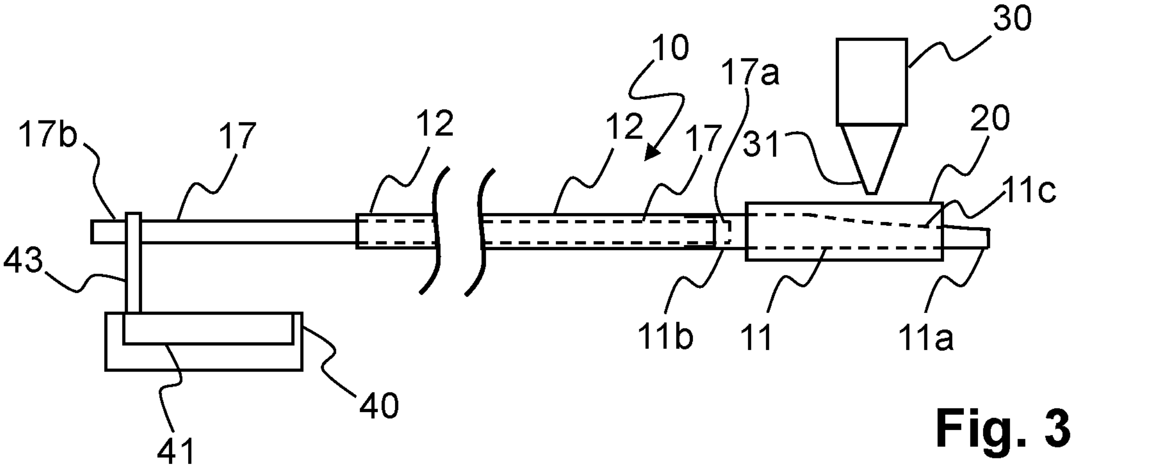
Figures 4, 5, 6:
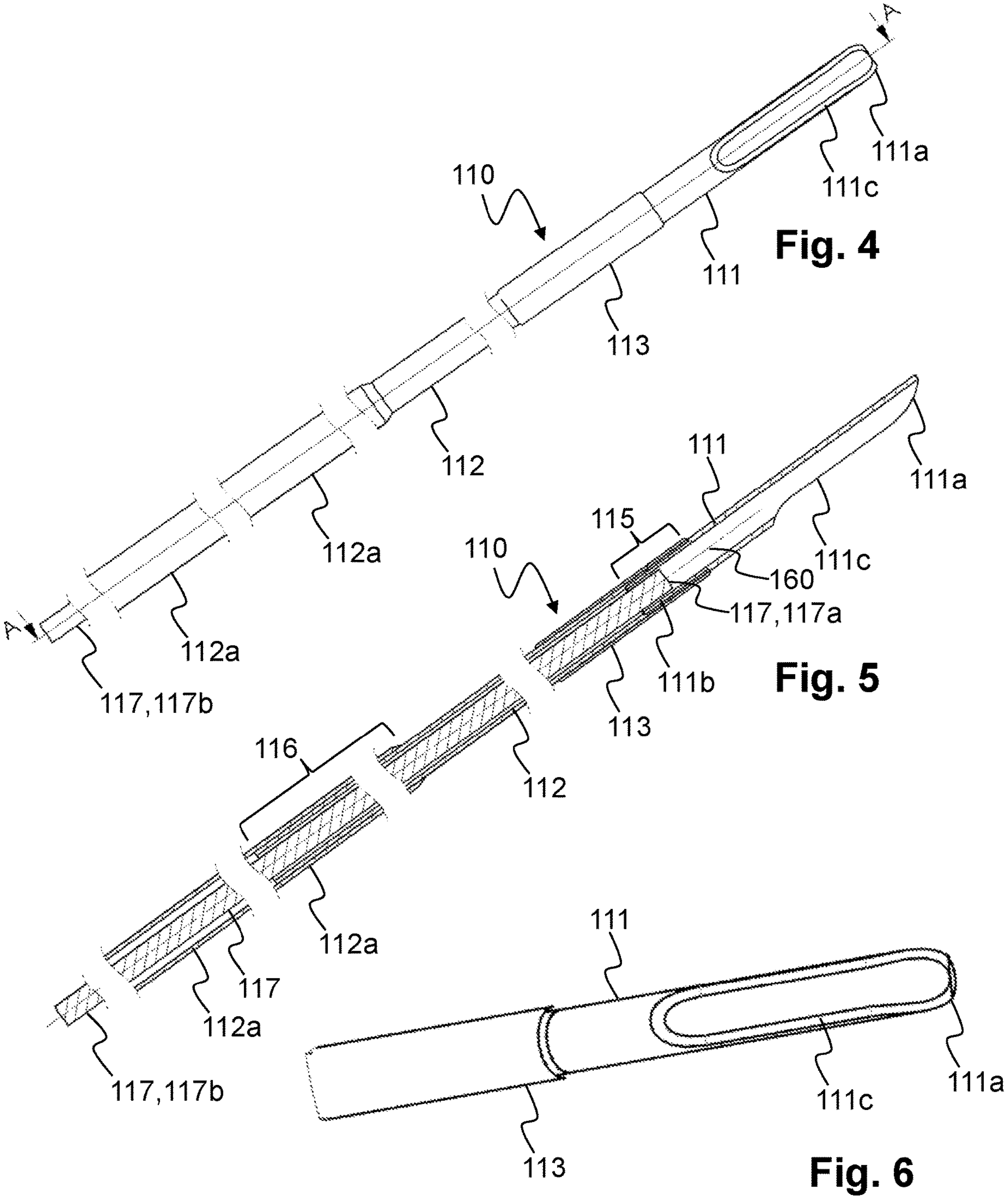
FIG. 4 shows a second embodiment of a beam block in a side view.
FIG. 5 depicts the embodiment of FIG. 4 in a longitudinal section along the arrows A-A shown in FIG. 4.
FIG. 6 shows the head section of the embodiment of FIG. 4 in a top view.
Figure 7:
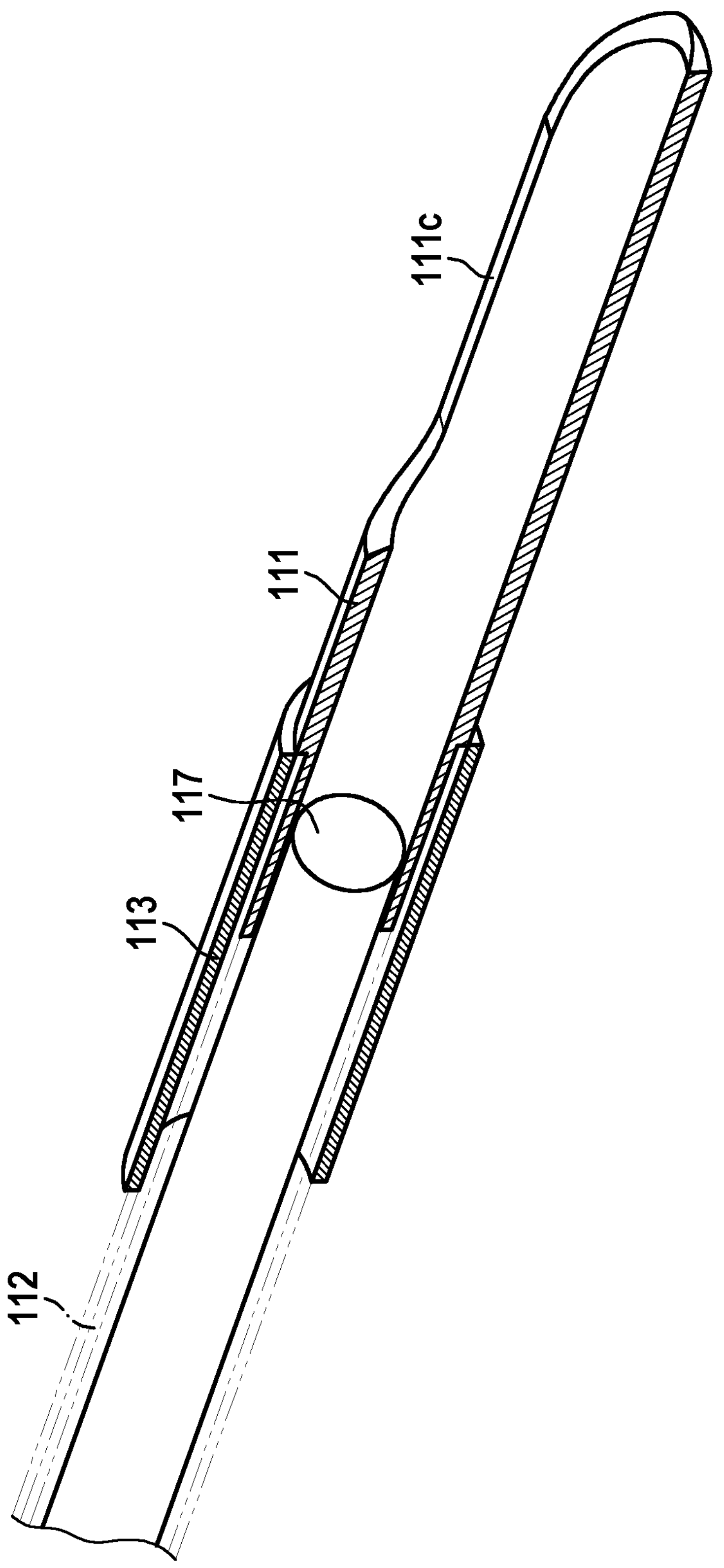
FIG. 7 depicts the head section and a part of the shaft section of the embodiment of FIG. 4 in a perspective view of a longitudinal section.

The laser cutting system shown in FIGS. 1 to 3 includes a beam block 10 and a semi-finished tubular product 20 which is cut by a laser 30 thereby producing a perforated tubular workpiece such as a stent. The beam block 10 includes a tubular head section 11 and a tubular shaft section 12, wherein the head section 11 is fixed to the shaft section 12 at its second end 11*b*. The head section 11 and the shaft section 12 of the beam block 10 extend along a longitudinal axis 60 and form a common inner cavity which accommodates a plunger element 17. One end of the beam block 10 is formed by the first end 11*a* of the head section 11. The head section 11 of the beam block 10 is located within the inner cavity of the semi-finished product 20 during lasering as shown in FIGS. 1 to 3. The laser 30, for example a μs-fiber laser, providing μs pulses, cuts through the wall of the semi-finished product 20 consisting, for example, of Nitinol using a melt cutting process. As a process gas, for example, argon is used producing the jet stream. The laser beam and the jet stream are directed onto the outer shell surface of the semi-finished product 20 from a radial direction (referred to the longitudinal direction represented by the longitudinal axis 60) for laser cutting, wherein the front end of a nozzle 31 of the laser cutter 30 has a pre-defined radial distance from the outer shell surface of the semi-finished product. By cutting perforations, structures like holes, webs, struts, wires or similar structures or any combination of such structures are formed in the wall of the semi-finished product.

The head section 11 further includes a recess 11*c* that is located at the first end 11*a* of the head section and extends from there into the direction of the second end 11*b*. The recess 11*c* is formed partly inclined and such that the wall of the tube of the head section 11 is removed on the upper side (if one refers to the view shown in FIGS. 1 to 3). The inclination is such that the removed part of the tube wall is greater at the first end 11*a* of the head section 11 than at the opposite end of the recess 11*c* (with regard to the longitudinal direction). As the tube wall is removed along the extension of the recess 11*c* the inner cavity of the tubular head section 11 is exposed and molten material 50 accumulates within the cavity as shown in FIG. 1.

The opposite end of the beam block 11 along the longitudinal direction represented by longitudinal axis 60 is formed by the second end 17*b* of the plunger element 17. The plunger element 17 further has a leading end (first end 17*a*) that is opposite to the second end 17*b* along the longitudinal direction. The plunger element 17 may consist of V2A steel, for example. In the initial state/position, the plunger element 17 extends from the second end 11*b* of the head section 11 to the end of the shaft section 12 opposite the head section 11 and further the plunger element 17 projects from the shaft section 12 of the beam block 10. There, at the second end 17*b*, the plunger element 17 is connected to a driving unit 40. In particular, the plunger element 17 is connected to a double acting pneumatic cylinder 41 of the driving unit 40 by a stiff arm 43. The pneumatic cylinder 41 drives the plunger element 17 via the arm 43 from an initial state/position shown in FIG. 1 into the direction of the first end 11*a* of the head section 11 and back into the initial position as shown in FIGS. 2 and 3, respectively, i.e. the plunger element 17 performs a reciprocating movement driven by the pneumatic cylinder 41.

FIG. 1 shows the initial state/position of the plunger element 17 in which the plunger element is retracted within the common inner cavity of the head section 11 and the shaft section 12 of the beam block. Driven by the pneumatic cylinder 41 of the driving unit 40 the front end 17*a* of the plunger element 17 is moved during a forward phase of the reciprocating movement along the longitudinal direction to the first end 11*a* of the head section 11 thereby scraping off the inner surface of the head section 11 and pushing the molten and accumulated material 50 of the semi-finished product 20 to and over the first end 11*a* of the head section 11 into a container (not shown) that collects the molten material 50. Then, during the backward phase of the reciprocating movement the plunger element 17 is driven by the pneumatic cylinder 41 into the opposite direction along the longitudinal axis 60, wherein at the end of the movement the plunger element 17 takes the initial position/state as shown in FIG. 3. The molten material 50 is removed. The duration of one reciprocating movement of the plunger element 17 (or the pneumatic cylinder 41) is, for example, between 1 s and 10 s. The reciprocating movement may be periodically repeated with a frequency, for example, in the range of 0.2 $min^{-1}$ to 0.0055 Hz.

At the end of the forward phase and the backward phase the movement of the pneumatic cylinder 41 and thereby the movement of the plunger element 17 may be damped, for example by a throttle check valve.

For manufacturing of a perforated tubular workpiece, e.g., a stent, at first the laser cutting system as described above and a semi-finished product 20 for such stent is provided. Then, at first the head section 11 of the beam block 10 is accommodated within the inner cavity of the semi-finished product 20. After correct positioning of the beam block 10 within the semi-finished product and the laser cutter 30 in relation to the semi-finished product 20, laser cutting starts using the laser cutter 30. During laser cutting the plunger element is periodically activated to provide the reciprocating movement thereby removing the molten material 50 accumulated within the inner cavity of the head section 11 of the beam block 10. During laser cutting, the laser cutter 30 may be moved relative to the outer shell surface of the semi-finished product 20.

The second embodiment of a beam block 110 depicted in FIGS. 4 to 7 basically corresponds to the beam block 10 of the first embodiment. Accordingly, the reference numbers of the second embodiment minus the number 100 correspond to the reference numbers of similar elements of the beam block of the first embodiment. With regard to these elements it is referred to the first embodiment. The driving unit and the arm connecting the plunger element 117 to the driving unit are not shown but similar to the first embodiment. However, one difference is that the shaft section of the beam block 110 includes two separate tubular parts, a first shaft section 112 and a second shaft section 112*a*. The first and the second shaft sections 112, 112*a* are fixed to each other by an adhesive connection within the section 116 of the beam block 110. The second shaft section 112*a* which is located further away from the head section 111 than the first shaft section 112 has a greater inner and outer diameter than the first shaft section 112.

As one can see more clearly from the second embodiment, the inner cavity of the head section 111 and the shaft section 112, 112*a* is a common cavity which has a slightly larger diameter than the outer diameter of the plunger element 117 so that the plunger element is allowed to reciprocate within this common cavity for removal of the molten material.

Further, the second embodiment of the beam block 110 includes a tubular sleeve 113 which is accommodated at the outer shell surface of head section 111 and the first shaft section 112 in the area where the head section 111 and the first shaft section are fixed to each other by an adhesive connection. This tubular sleeve 113 is fixed to the outer surface of the head section 111 and the first shaft section 112 by an adhesive connection, as well. The tubular sleeve 113 consists of, for example, PTFE thereby providing a non-stick shell surface. This allows easy sliding of the whole beam block 110 within a holding groove, for example, during introduction within the semi-finished product. In one embodiment, the beam block 110 may include not only the one tubular sleeve with the non-stick shell surface shown in FIGS. 4 and 5 but two or more of such sleeves along the full length of the beam block.

Additionally, the second embodiment shows one example of the recess 111*c* at the first end 111*a* of the head section 111 of the beam block 110. It is clearly shown in FIGS. 4 to 7 that at the recess 111*c* the wall of the tubular head section 111 is removed on one side thereby exposing the inner cavity of the head section 111 for accumulation of the molten material. In the center section, the edge of the recess 111*c* runs approximately parallel to the longitudinal direction, whereas at the first and second end of the recess 111*c* the edges are inclined with regard to the longitudinal direction.

As indicated above, the removal of the molten workpiece material by the plunger element of the beam block during laser cutting considerably reduces production costs as the perforated workpiece reject rate is significantly decreased.

The invention claimed is:

1. A beam block for laser cutting to produce a perforated tubular workpiece, comprising:

a tubular head section configured to be accommodated within an inner cavity of a semi-finished product during laser cutting, wherein the tubular head section comprises a recess at a first end of the tubular head section, the recess configured to accept molten workpiece material into an inner surface of the tubular head section, a wall of the first end of the tubular head section being removed on one side along an extension of the recess to form a removed part of the tubular head section that exposes an inner cavity of the tubular head section, a shaft section located at a second end of the tubular head section, and a plunger configured to be reciprocated along the inner cavity of the tubular head section to the first end of the tubular head section to thereby eject molten workpiece material from the removed part of the tubular head section.

2. The beam block of claim 1, wherein the plunger comprises a wire shape.

3. The beam block of claim 1, wherein the plunger is driven by a driving unit, the driving unit being one of a pneumatic driving unit, an electric driving unit or a hydraulic driving unit.

4. The beam block of claim 1, wherein the shaft section comprises a tubular form and the plunger element reciprocates along the shaft section.

5. The beam block of claim 1, comprising a tubular sleeve accommodated at a part of a shell surface of the tubular head section, wherein the shell surface comprises a non-stick shell surface.

6. A laser cutting system comprising the beam block of claim 1 and a laser cutter, wherein the tubular head section of the beam block is configured to be accommodated within a tubular semi-finished product to be cut by the laser cutter, wherein a nozzle of the laser cutter is configured to be located within a pre-defined radial distance from an outer shell surface of the semi-finished product.

7. The laser cutting system of claim 6, wherein the laser cutter comprises a laser providing us pulses.

8. The laser cutting system of claim 7, wherein the laser operates with argon as a high-pressure gas.

9. An operation method of the beam block of claim 1, comprising:

receiving molten workpiece material into the inner surface of the tubular head section; and reciprocating the plunger along the inner cavity of the tubular head section to the first end of the tubular head section, thereby ejecting the molten workpiece material from the inner surface of the tubular head section.

10. The operation method according to claim 9, wherein the reciprocating comprises periodic movement in a frequency in the range of 0.2 $min^{-1}$ to 0.0055 Hz.

11. The operation method according to claim 9, wherein a duration of one reciprocating movement of the plunger is in the range of 0.5 s to 10 s.

12. The operation method according to claim 11, wherein the duration is in the range of 0.5 s to 1.5 s.

13. A manufacturing method for making a perforated tubular workpiece from a tubular semi-finished product using the laser cutting system of claim 6, comprising:

placing the beam block within the semi-finished product such that the semi-finished product is located at an area of the first end of the tubular head section, and laser cutting the semi-finished product using the laser cutter.

14. The manufacturing method according to claim 13, comprising reciprocating the plunger periodically during the laser cutting.

15. A beam block for laser cutting to produce a perforated tubular workpiece, comprising:

a tubular head section configured to be accommodated within an inner cavity of a semi-finished product during laser cutting, wherein the tubular head section comprises a recess at a first end of the tubular head section, the recess configured to accept molten workpiece material into an inner surface of the tubular head section, a shaft section located at a second end of the tubular head section, and a plunger configured to be reciprocated along an inner cavity of the tubular head section to the first end of the tubular head section to thereby eject molten workpiece material from the inner surface of the tubular head section, wherein the plunger is driven by a driving unit, the driving unit being one of a pneumatic driving unit, an electric driving unit or a hydraulic driving unit, and wherein the driving unit comprises a damping component configured to damp the plunger element movement at the end of at least one of a forward movement phase and a backward movement phase of the plunger.

16. A beam block for laser cutting to produce a perforated tubular workpiece, comprising:

a tubular head section configured to be accommodated within an inner cavity of a semi-finished product during laser cutting, wherein the tubular head section comprises a recess at a first end of the tubular head section, the recess configured to accept molten workpiece material into an inner surface of the tubular head section, a shaft section located at a second end of the tubular head section, and a plunger configured to be reciprocated along an inner cavity of the tubular head section to the first end of the tubular head section to thereby eject molten workpiece material from the inner surface of the tubular head section, wherein the tubular head section is fixed to the shaft section by an adhesive joint.

17. An operation method of a beam block for laser cutting to produce a perforated tubular workpiece, the beam block comprising:

a tubular head section configured to be accommodated within an inner cavity of a semi-finished product during laser cutting, wherein the tubular head section comprises a recess at a first end of the tubular head section, the recess configured to accept molten workpiece material into an inner surface of the tubular head section, a shaft section located at a second end of the tubular head section, and a plunger configured to be reciprocated along an inner cavity of the tubular head section to the first end of the tubular head section to thereby eject molten workpiece material from the inner surface of the tubular head section, the operation method comprising:

receiving molten workpiece material into the inner surface of the tubular head section and reciprocating the plunger along the inner cavity of the tubular head section to the first end of the tubular head section, thereby ejecting the molten workpiece material from the inner surface of the tubular head section, and damping movement of the plunger at an end of at least one of a forward movement phase and a backward movement phase of the reciprocating.

* * * * *